US00PP13759P39

(12) United States Plant Patent
Fear

(10) Patent No.: US PP13,759 P3
(45) Date of Patent: May 6, 2003

(54) BLACKBERRY PLANT NAMED 'ZORRO'

(75) Inventor: Carlos D. Fear, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 66 days.

(21) Appl. No.: 09/772,327

(22) Filed: Jan. 29, 2001

(65) Prior Publication Data

US 2002/0144322 P1 Oct. 3, 2002

(51) Int. Cl.[7] ..... A01H 5/00
(52) U.S. Cl. ..... Plt./203

(58) Field of Search ..... Plt./203

*Primary Examiner*—Bruce R. Campell
*Assistant Examiner*—June Hwu
(74) *Attorney, Agent, or Firm*—Pennie & Edmonds LLP

(57) ABSTRACT

The present invention relates to a nerw and distinct cultivar of blackberry plant named 'Zorro'. The new cultivar is distinguished from other blackberry cultivars by its high productivity, early season, and low chill requirement. 'Zorro' produces fruit with improved quality and shipping characteristics over a long fruiting period. The new cultivar is distinguished from its seed parent by having better flavored fruit; it is distinguished from its pollen parent by its larger fruit.

3 Drawing Sheets

LATIN NAME OF THE GENUS AND SPECIES OF THE PLANT CLAIMED

Rubus hybrid

VARIETY DENOMINATION

'Zorro'.

1. BACKGROUND OF THE INVENTION

This invention relates to a new cultivar of blackberry called 'Zorro'. The new cultivar was developed from hybridization of the unpatented female cultivar 'By59.2' with the unpatented male selection 'B46.1'. The parents were crossed in Spring 1994 whereafter fruit and seed were collected to produce seedlings for field planting in Watsonville, Calif. in 1994. The new cultivar was selected in 1996 for its good flavor and early season of ripening. The cultivar was asexually propagated in Watsonville, Calif., and reproduced true to type plants by in vitro shoot tip culture.

2. SUMMARY OF THE INVENTION

The present invention provides a new and distinct blackberry cultivar named 'Zorro'. The variety is botanically identified as Rubus L. subgenus Rubus. The variety is a complex Rubus hybrid, which can be characterized as an erect tetraploid with considerable *R. allegheniensis* background with other species such as *R. trivialis, R. argutus* and *R. ulmifolius* also appearing in its background. The new cultivar produces a floricane crop which begins in mid-May and continues until mid-August. The new blackberry variety is distinguished from other varieties by a number of characteristics as set forth in Table 1. In particular, the new cultivar is distinguished by its early season, its low chill requirement, and its improved quality and shipping characteristics. Yield of the new cultivar is high when compared to many other varieties. There have been no observed plant or fruit diseases and no observed pest resistance or susceptibility. The variety has been developed for fresh market shipping use, and has performed well in coast-to-coast shipping tests and held up well after cold storage at 34 degrees Fahrenheit for periods of up to ten days.

3. COMPARISION TO SIMILAR VARIETIES

The variety that we believe to be similar to 'Zorro' from those known to us is 'Olallie', an unpatented variety. 'Zorro' is particularly different from 'Olallie' by being slightly later ripening, having less postharvest color reversion, having less acidic flavor, and having better fruit firmness. Further detailed comparison of 'Zorro' to 'Olallie' and 'Chester' is presented in Table 1.

BRIEF DESCRIPTION OF THE DRAWINGS

The accompanying photographs show typical specimens of the fruit, leaves and shoot of the new cultivar, in color as nearly true as reasonably possible in color illustrations of this type.

5. DESCRIPTION OF THE NEW VARIETY

Figure 1:
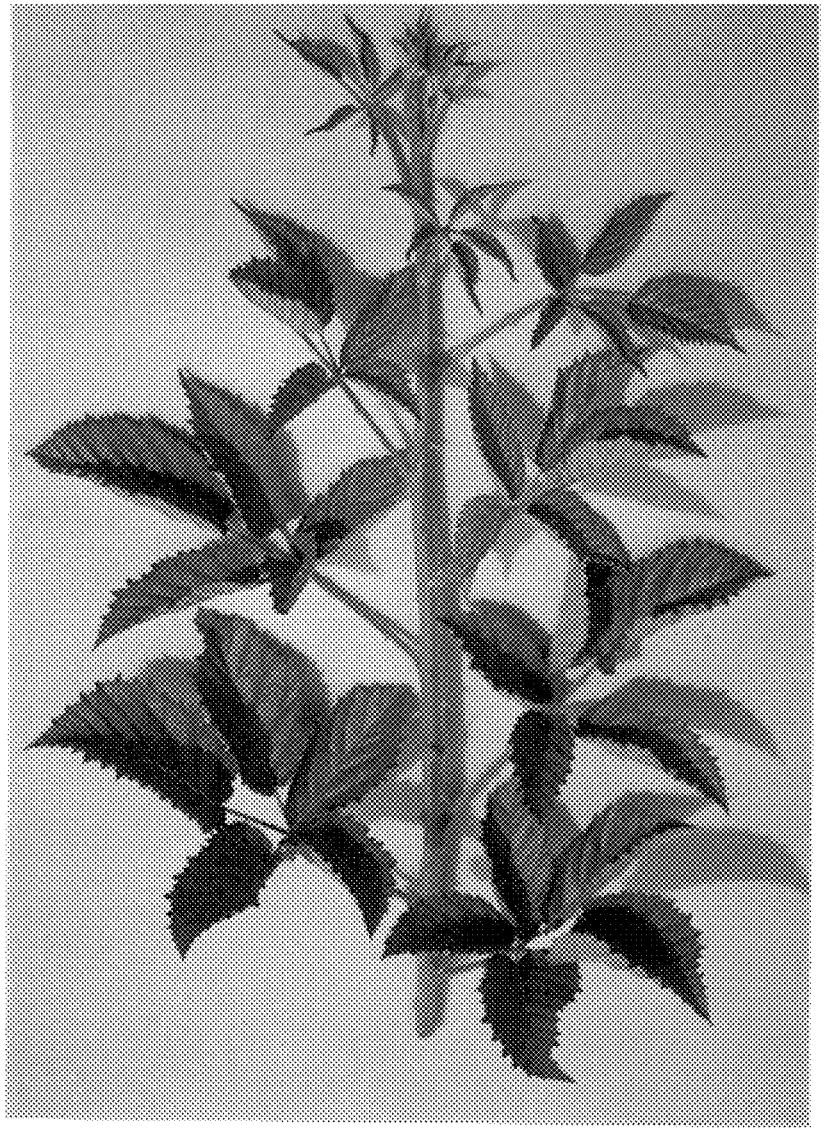
FIG. 1 is a photograph showing a primocane shoot, mature leaf and stem of 'Zorro'.
Figure 2:
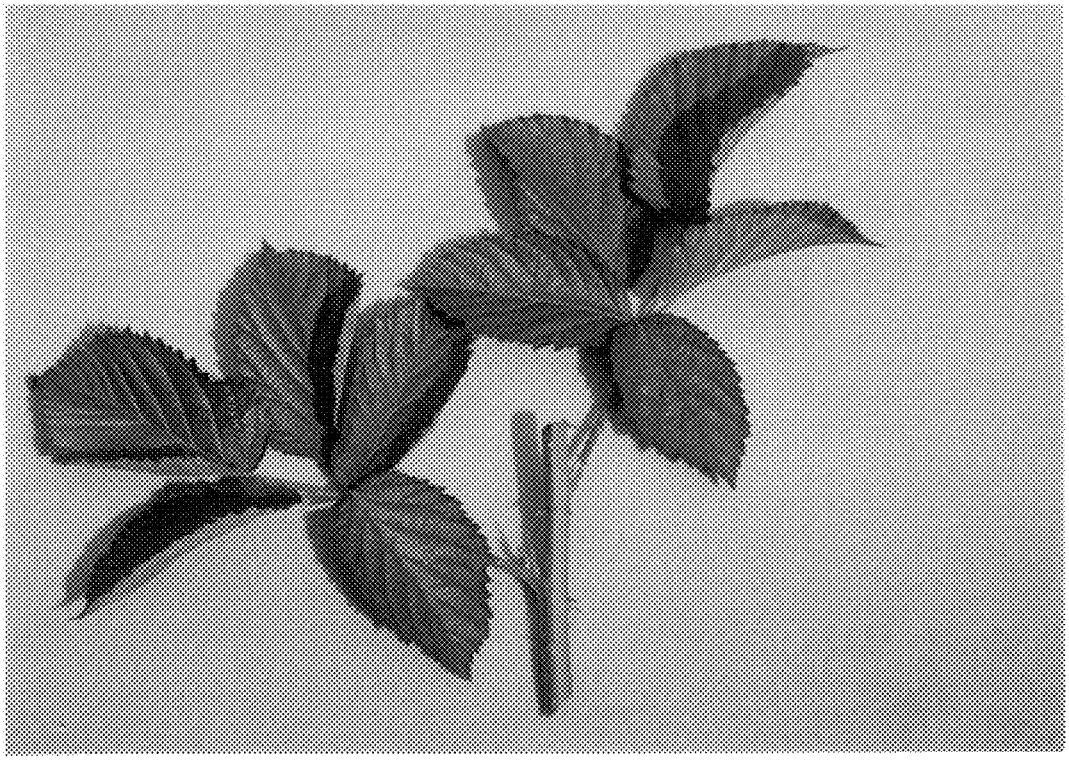
FIG. 2 is a photograph showing a close-up view of a primocane shoot, mature leaf and stem of 'Zorro'.
Figure 3:
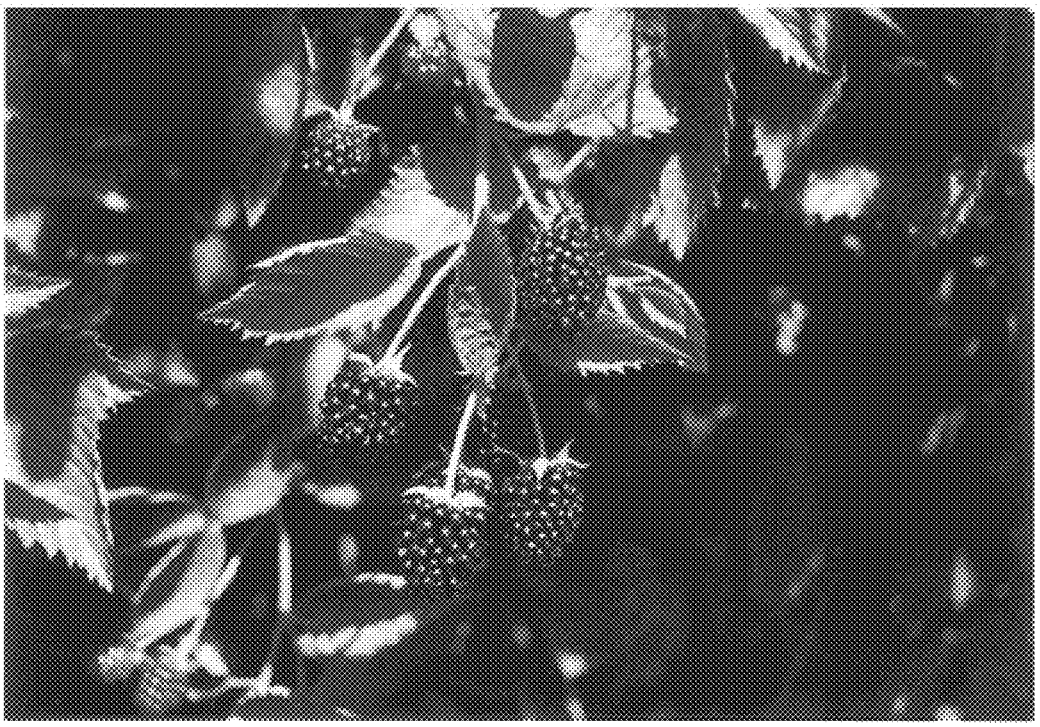
FIG. 3 is a photograph of a 'Zorro' fruiting lateral with fruit in various stages of development.

The following detailed description of the new blackberry cultivar, 'Zorro', is based upon recorded observations of plants on two to five years old grown using commercial growing practices in Watsonville, Calif. and is believed to apply to plants of the 'Zorro' cultivar grown in similar conditions of soil and climate elsewhere. Plants were planted on soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

5.2 CHARACTERISTICS OF THE NEW VARIETY

Table 1 provides information on the plant and fruit characteristics of the new blackberry cultivar 'Zorro' compared with characteristics of the blackberry cultivars 'Olallie' (non-patented) and 'Chester' (non-patented). Both 'Olallie' and 'Chester' are currently important cultivars for fresh market shipping, and this are comparable to the proposed use of the new invention, 'Zorro'. Observations of 'Zorro' and 'Olallie' were taken in side-by-side comparison in 1999 and in 2000.

Fruit of the new cultivar is particularly characterized and distinguished from other cultivars by its improved flavor and shipping characteristics. Drupelets of 'Zorro' fruit show slightly less postharvest color reversion compared to 'Olallie', the most comparable cultivar fruiting at the same time of the season.

'Zorro' is highly productive and produces most of its crop in the early part of the harvest season. The fruit yield of 'Zorro' is medium, averaging around 19,400 lbs per acre in comparison to the fruit yield of 'Olallie' which averages around 21,000 lbs per acre. Canes of 'Zorro' are vigorous, thorny and have buds with a low chill requirement. The bud break of 'Zorro' is in late March and usually 1 week before 'Olallie'. The average cane length for 'Zorro' under a normal growing season is 8.5 feet and the average cane length for 'Chester' is 9 feet. The primocane color on the exposed side of the cane is 183C and 144A on the shaded side. Floricanes are 146C on the exposed side and 144A on the shaded sided.

The spines or prickles average 5.5 mm in length. Prickle color on the exposed side is 183B and N144B on the shaded side. The leaf has very minor undulations between where the veins are. The leaf surface has small, soft hairs on both the upper and lower leaf surface. The petiole color is 183C. The sepal color is 138B. The petal color is 155C. The pedicel length averages 27 mm under normal condtions.

'Zorro' is distinguished from its pollen parent, 'B46.1', by having larger fruit. 'Zorro' is distinguished from its seed parent, 'B59.2', by being thorny and having better flavored fruit.

TABLE 1

PLANT CHARACTERISTICS OF 'ZORRO'

| | 'Zorro' | 'Olallie' | 'Chester' |
|---|---|---|---|
| GENERAL | | | |
| Vigor | moderate–high | moderate–high | high |
| Growth habit | semi-upright | trailing | semi-upright |
| Productivity | high | high | high |
| Self fruitfulness | yes | yes | yes |
| Number of young shoots | medium | medium | medium |

TABLE 1-continued

PLANT CHARACTERISTICS OF 'ZORRO'

| | 'Zorro' | 'Olallie' | 'Chester' |
|---|---|---|---|
| CANES | | | |
| Primocanes | | | |
| Anthocyanin coloration | present | present | present |
| Spines | present | present | absent |
| color | green | purple | — |
| attitude of tip | downward | horizontal | — |
| texture | rigid | heavy | — |
| presence and distribution on petioles | present; irregularly distributed | present; irregularly distributed | absent |
| density in central third of shoot | medium | medium | — |
| Internodal distance (cm) - central third of mature cane | 2.5 | 2.6 | 3.1 |
| Glaucosity on full grown shoot | absent to very weak | weak | weak |
| Strength of full grown shoot | medium | medium | strong |
| Cane cross section | angular to grooved | rounded to angular | angular to grooved |
| LEAVES | | | |
| Relief between veins | weak | medium | medium |
| Number of leaflets | usually 5 | usually 3 | usually 5 |
| Leaf color | medium | medium | light |
| upper side | 137A, 137B | 137A, 137B | 147A |
| underside | 137C, 138A | 147B | 146A |
| Glossiness of upper surface | medium | medium | dull |
| Leaf cross section | concave | concave-flat | concave |
| Terminal leaflet | | | |
| length (cm) | 10.3 | 8.9 | 11.1 |
| width (cm) | 7.6 | 7.6 | 9 |
| shape | ovate | cordate | cordate |
| tip | acute | acuminate | acuminate |
| base | acute | cordate | cordate |
| margin | double serrate | double serrate | double serrate |
| Lateral leaflet | | | |
| overlap of lateral leaflets | free to touching | overlapping | overlapping |
| length (cm) | 9.9 | 8.7 | 10.2 |
| width (cm) | 6.3 | 6.1 | 7.1 |
| shape | ovate | ovate | ovate |
| tip | acuminate | acuminate | acute |
| base | acute | acute | acute |
| margin | double serrate | double serrate | serrate |
| Petiole | | | |
| mean length (cm) | 8.4 | 5.3 | 7.9 |
| range | 5.2–10.6 | 3.6–8.7 | 3.9–10.2 |
| pigmentation of upper surface | reddish | green - slightly pink | purple |
| pigmentation of underside | green | green - slightly pink | green - pinkish |
| Length of stalklet | short | very short | medium |
| Rachis length (cm, between terminal and adjacent lateral leaflets) | 3.6 | 2.8 | 3.1 |
| Stipule orientation | erect | variable; clasping to erect | erect |
| FLOWERS | | | |
| Time of bud burst | early | early | late |
| Time of beginning of flowering | early | early | late |
| Flower size | medium to | small to | small to |

TABLE 1-continued

| PLANT CHARACTERISTICS OF 'ZORRO' | 'Zorro' | 'Olallie' | 'Chester' |
|---|---|---|---|
| | large | medium | medium |
| Petal size | | | |
| length (mm) | 19.1 | 16.5 | 18.3 |
| width (mm) | 12.4 | 11.7 | 10.9 |
| Anthocyanin color of pedicel | absent | absent | present |
| Intensity of pedicel coloration | — | — | weak |
| Length of pedicel | medium to long | long | short |
| Flower number (third node from tip of lateral) | 5.8 | 3.6 | 2 |
| FRUIT | | | |
| Harvest season | early | early | mid to late |
| Dimensions weight (g/fruit) | 4.2 | 5.2 | 3.2 |
| size | medium | medium | small |
| length (cm) | 2.7 | 3.3 | 1.9 |
| width (cm) | 2.1 | 1.4 | 1.9 |
| Fruiting lateral length (in mid cane) | medium | medium | medium - long |
| Mean number of fruit per lateral | 7.7 | 6.2 | 22.8 |
| range | 5–20 | 3–9 | 17–40 |
| Shape | ovate to elliptic; longer than broad | narrow ovate; much longer than broad | round to ovate; as long as broad |
| Color | black | purple-black to black | black |
| immature | 184A | 178A–183B | 184A |
| maturing | 187A | 187A | 200A–202A |
| mature | 200A | 200A | 202A |
| Firmness | firm | medium | firm |
| Glossiness | strong | medium - strong | medium |
| Soluble solids | 9.6 | 9.7 | 9.9 |
| Titratable acidity (% as citric acid) (ml of added .1 N NaOH to pH 8.1) | 9 | 13.3 | 9.9 |
| Number of drupelets per fruit | 85 | 86.12 | 40 |

Table 2 provides information on the seed weight of the new blackberry cultivar 'Zorro' compared with characteristics of the blackberry cultivars 'Olallie' (non-patented) 'Chester' (non-patented), 'Sleeping Beauty' application Ser. No. 09/772,329), 'Pecos' (application Ser. No. 09/772,211) and 'Sonoma'.

TABLE 2

| Cultivar | Seed Weight |
|---|---|
| 'Zorro' | 2.3 mg |
| 'Olallie' | 2.1 mg |
| 'Chester' | 3.5 mg |
| 'Sleeping Beauty' | 4.1 mg |
| 'Pecos' | 3.5 mg |
| 'Sonoma' | 3.4 mg |

5.2 NUCLEIC ACID FINGERPAINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531-5). Using a variety of oligonucleotide primers, alone or in combination, RAPD analysis of 'Zorro' 'Chester', and 'Olallie' yielded DNA fragment patterns that uniquely distinguish each of these genetically distinct genotypes.

We claim:

1. A new and distinct cultivar of blackberry plant, substantially as shown and described.

* * * * *